US 6,833,108 B2

(12) United States Patent
Laub et al.

(10) Patent No.: US 6,833,108 B2
(45) Date of Patent: *Dec. 21, 2004

(54) METHOD AND APPARATUS FOR INACTIVATING CONTAMINANTS IN BLOOD PRODUCTS

(75) Inventors: Ruth Laub, Brussels (BE); Luc De Wael, Ranst (BE); Mario Di Giambattista, Braine-le-Comte (BE)

(73) Assignee: Department Central de Fractionnement de la Croix-Rouge SCRL, Brussels (BE)

(*) Notice: Subject to any disclaimer, the term of this patent is extended or adjusted under 35 U.S.C. 154(b) by 587 days.

This patent is subject to a terminal disclaimer.

(21) Appl. No.: 09/747,161

(22) Filed: Dec. 22, 2000

(65) Prior Publication Data

US 2001/0046450 A1 Nov. 29, 2001

Related U.S. Application Data

(63) Continuation-in-part of application No. 08/983,294, filed as application No. PCT/BE96/00076 on Jul. 15, 1996, now Pat. No. 6,190,608.

(30) Foreign Application Priority Data

Jul. 14, 1995 (WO) .............................. PCT/BE95/00069

(51) Int. Cl.[7] .............................................. A61K 41/00
(52) U.S. Cl. ................ 422/24; 250/492.1; 250/455.11; 422/186; 422/186.3
(58) Field of Search ...................... 422/24, 186, 186.3; 250/492.1, 455.11; 514/2; 530/382, 383

(56) References Cited

U.S. PATENT DOCUMENTS 4,297,344 A 10/1981 Schwinn et al.
5,099,003 A 3/1992 Kotitschke et al.
5,133,932 A 7/1992 Gunn et al.
5,834,420 A 11/1998 Laub et al.
6,190,608 B1 * 2/2001 Laub et al. .................... 422/24

FOREIGN PATENT DOCUMENTS

| EP | 0 018 561 B1 | 4/1980 |
|---|---|---|
| EP | 0 018 561 A2 | 4/1980 |
| EP | 0 311 950 A2 | 10/1988 |
| JP | 07196531 A | 8/1995 |
| WO | WO 94/03054 A1 | 2/1994 |
| WO | WO 94/28120 A1 | 12/1994 |
| WO | WO 95/00631 A1 | 1/1995 |
| WO | WO 96/02571 A1 | 2/1996 |

OTHER PUBLICATIONS

Gerard Marx et al., *Protecting Fibrinogen with Rutin during UVC Irradiation for Viral Inactivation*, Photochemistry and Photobiology, 63(4):541–546, 1996.

Hart et al., *Inactivation of Viruses during Ultraviolet Light treatment of Human Intravenous Immunoglobulin and Albumin*, Vox Sang, 64:82–88, 1993.

Chin et al., *Virucidal Short Wavelength Ultraviolet Light Treatment of Plasma and Factor VIII Concentrate: Protection of Proteins by Antioxidants*, Blood, 86(11):4331–4336, 1995.

* cited by examiner

Primary Examiner—Krisanne Thornton
(74) Attorney, Agent, or Firm—Knobbe, Martens, Olson & Bear LLP (57) ABSTRACT

A method and an apparatus for inactivating contaminants in blood products are disclosed. The blood product is flowed past an emitter of type C ultraviolet radiation while controlling the flow of the blood product so that the irradiation doses which are received by the blood product are lower than 640 joules/m$^2$. The blood product is substantially free of nonenveloped viruses after the irradiation. The apparatus includes an emitter of type C ultraviolet radiation placed so as to emit the type C radiation toward the blood product in a quartz tube or a tube made of polymerized material which does not absorb type C radiation. The apparatus also includes a flow meter for controlling the flow rate of the blood product to be treated.

31 Claims, 6 Drawing Sheets

METHOD AND APPARATUS FOR INACTIVATING CONTAMINANTS IN BLOOD PRODUCTS

RELATED APPLICATIONS

This application is a continuation-in-part of Application No. 08/983,294, filed Mar. 23, 1998 now U.S. Pat. No. 6,190,608, which is the U.S. national phase under 35 U.S.C. §371 of International Application No. PCT/BE96/00076, filed Jul. 15, 1996, which claims priority to PCT/BE95/00069, filed Jul. 14, 1995.

OBJECT OF THE INVENTION

The present invention relates to a method for inactivating contaminants in blood products, especially whole blood, plasma, fluids comprising cellular blood compounds, and blood derivatives such as clotting factors (factor VIII, factor IX, factor VII, factor II, Factor X, von Willebrand's factor and the like), fibrinogen, fibronectin, immunoglobulins, albumin, thrombin, anti-thrombin III, plasminogen, and the like, including nonnatural products obtained by biological engineering, as well as the apparatus for carrying out the said method.

The present invention also relates to blood products treated by the method of the invention as well as pharmaceutical and/or cosmetic compositions comprising the said blood products.

TECHNOLOGICAL BACKGROUND OF THE INVENTION

The availability of blood products requires, for their use for therapeutic or nontherapeutic purposes, purification techniques which make it possible to obtain products of high purity, and preferably free of contaminants, in particular of viral contaminants.

In blood products, the viral contaminants may be enveloped viruses (HIV, hepatitis B, C, D, E and G viruses, and the like) or nonenveloped viruses (hepatitis A virus, parvovirus, and the like).

For many years, various international or national bodies have introduced increasingly strict standards for the preparation of blood products so as to prevent their application for therapeutic or nontherapeutic purposes when they contain viral contaminants (Council Directives 65/65 EEC, 75/319/EEC & 89/381 EEC).

At the European level, the CPMP standards (CPMP/BWT 268/95 and CPMP/BWP/269/95 rev 2) require the use of certain treatments against enveloped or nonenveloped viruses.

It is in particular mentioned in these documents that an inactivation step using heat (dry or steam) or using pasteurization in the preparation of clotting factors is effective against the hepatitis A virus, but would not be very effective against other nonenveloped viruses, in particular parvoviruses.

On the other hand, a treatment comprising a chemical inactivation step (by addition of solvents-detergents) is effective for enveloped viruses but ineffective for treating nonenveloped viruses.

It is also known to use certain chemical agents such as beta-propiolactone, which is effective in the treatment of nonenveloped viruses but has the disadvantage of modifying the treated proteins.

It is also known that certain long treatments using pH modification, below pH 4, or the addition of proteases allows inactivation of some nonenveloped viruses such as parvovirus to a reduced extent. However, these treatments also modify the conformation and structure of the treated proteins.

Consequently, it is known that, to date, the majority of the physicochemical treatment steps capable of being used to obtain viral inactivation of blood products are either highly toxic, or unacceptably affect the conformation of the treated proteins, or are ineffective for treating nonenveloped viruses, in particular parvoviruses.

Parvoviruses are small nonenveloped DNA viruses which infect numerous animal species, including man (Handbook of Parvoviruses, Vol. 1, pp. 1–30, Disinfection, Sterilization and Preservation, Fourth Edition, Seymour S. Block, Ed. Lea & Febiger, Philadelphia-London). They are endemic in nature and cause a wide variety of diseases.

Among these, parvovirus B19 is the only known member of the Parvoviridae family which is pathogenic for man. Likewise, murin parvovirus H1 can also infect man.

Parvovirus B19 infection in a healthy man may be asymptomatic or may induce benign diseases (example: fifth disease in children).

On the other hand, in immunodeficient patients or patients suffering from blood disorders, it may lead to chronic anaemias and to transient aplasias which may be associated with haemolytic anaemias.

Furthermore, Parvovirus B19 infection induces apoptosis of erythroid cells in vitro and in vivo (Yaegashi et al, Journal of Infection, Vol. 39, pp. 68–76 (1999).

Passing through the placenta, it may cause intrauterine death. It exhibits a remarkable tropism for the erythroid lines of human haematopoietic progenitor cells.

A recent epidemiological survey has shown that 50 to 60% of the adult French population and 36% of 1- to 15-year-old children have a positive parvovirus serology.

The process of viral DNA has been demonstrated by genetic amplification (PCR) in a number of batches of purified factor VIII concentrates, regardless of the methods of viral inactivation used.

This has been confirmed by the B19$^+$ serology detection, without clinical sign, in 85% of haemophilic children who have received, since birth, only highly purified factor VIII concentrate (FVIII THPSD) used in France since 1988, free of any contamination with enveloped viruses (HIV, HBV, HCV) (Y. Lauriau et al., ler congrès de la Société Francaise de Transfusion [1st conference of the French Transfusion Company] (1994)).

This observation indeed demonstrates that, without new methods of viral inactivation, targeted at the selective elimination of parvoviruses, in particular of parvovirus B19, from blood products, the probability of contamination is high.

Parvoviruses are extremely resistant, even at high temperature. Their haemagglutination properties and their infectivity are not affected by chemical treatments, such as chloroform or various acids, and most resist enzymatic digestions, using RNase, DNase, papain or trypsin.

State of the Art

International Patent Application WO95/00631 describes a method of viral inactivation of blood products comprising the addition to these blood products of products which are photoactivable by UVA radiation and which would become toxic for the viruses present in these blood products. This method comprises a step which makes it possible to isolate these toxic reagents from the blood products so that the latter are not contaminated with these toxic agents.

Among these toxic agents, psoralen may be mentioned in particular.

However, this method has the disadvantage that it cannot be guaranteed that the treated blood products will not be completely free of these photoactivable agents which would be capable of denaturing and/or inactivating the treated blood products and causing toxicity in man or animals when they are reinjected repeatedly, even at a low dose, with the treated blood products.

It is also known that it is possible to sterilize a large number of products by subjecting them to ultraviolet radiation. It is in particular known from the document "Sterilization by Ultraviolet Irradiation" (chapter 31, IL SHECHMETSTER) that ultraviolet radiation is capable of destroying contaminants such as viruses, mycoplasmas, bacteria and fungi. Such a radiation may be used in particular in media such as gases or liquids.

It is also known from the document by Chin S. et al. (Blood, volume 86, No. 11, December 1995, p. 4331–4336) to treat blood products with type C ultraviolet radiation in the presence or in the absence of antioxidants such as rutin and to obtain the inactivation of nonenveloped viruses, particularly parvoviruses.

In addition, the methods of viral inactivation of the state of the art can affect the integrity and the activity of blood products (in particular the three-dimensional conformation of clotting factors such as factor VIII) and consequently their activities.

Furthermore, the methods of viral inactivation of the state of the art often exhibit difficulties in relation to their validation, because they exhibit problems of reproducibility or of monitoring. Indeed, certain treatment parameters must be modified or cannot be easily maintained, in particular when the degree of humidity has to be monitored if a treatment is carried out with dry heat. Furthermore, it is difficult to control the various steps of the operating procedures.

Aims of the Invention

The present invention aims to obtain a new method and an apparatus for inactivating contaminants present in blood products, which do not exhibit the disadvantages of the state of the art and which are simple, rapid, inexpensive and reproducible.

Another aim of the present invention is to develop a method of viral inactivation which preserves the integrity of blood products, including cells, in particular that of clotting factors such as factor VIII, factor IX, factor VII, factor II, factor X, von Willebrand's factor, fibronectin, fibrinogen, albunin, immunoglobulin, thrombin, anti-thrombin II, plasminogen LDL, lymphokines, interferons and the like.

A further aim of the present invention is to obtain a method and an apparatus which can be easily validated and which are in accordance with good pharmaceutical manufacturing practices (GMP) and with European standards (CPMP).

A last aim of the present invention is to obtain a method and an apparatus for viral inactivation of blood products which make it possible to inactivate enveloped viruses or nonenveloped viruses, preferably single-stranded, viruses such as parvoviruses, in particular parvoviruses B19 and H1 or HAV. The present invention also airs to obtain the said blood products tree of the said contaminants, in particular of nonenveloped viruses such as parvoviruses, in particular parvoviruses B19 and H1, without the activity of the blood product being affected.

Characteristic Features of the Invention

The present invention relates to a new method of inactivating parvoviruses, in particular parvoviruses B19 and H1, present in a blood product, according to which the said blood product is subjected to one or more emission(s) of type C ultraviolet radiation.

"Blood product" is understood to mean any blood product or a mix of blood protein compounds, under liquid or solid form, obtained naturally from the human or animal body or by the synthesis route (including genetic engineering) such as whole blood, its cellular compounds (such as erythrocytes, lymphocytes, monocytes and thrombocytes), its derivatives such as serum or plasma and blood protein compounds, namely clotting factors (factor VIII, factor IX, factor VII, factor II, factor X, von Willebrand's factor and the like), fibrinogen, fibronectin, immunoglobulins, albumin, thrombin, anti-thrombin II, plasminogen, LDL, lymphokines, interferons and the like, including protein compounds obtained by biological engineering, such as recombinant proteins or synthetic peptides.

These products may also be factors produced by certain specific blood cell lines, such as interferons, interleukins, or cell receptors, for these molecules obtained naturally or by the synthetic route, particularly the recombinant peptides or proteins obtained by the recombinant DNA technique. Advantageously, this method also causes inactivation of other contaminating agents such as nonenveloped viruses (HAV), enveloped viruses (HIV, hepatitis B, C, D, E and G viruses and the like), bacterial or fungi, including yeast agents and the like, which may be present in the blood product.

The method according to the invention may also be combined with one or more additional treatment(s) for inactivation of contaminants, particularly viral contaminants, well known to persons skilled in the art, in particular physical or chemical viral inactivation treatments chosen from the group consisting of one or more dry or wet heating step(s), the addition of chemical components, in particular of solvent-detergent or products which become active under ultraviolet radiation, one or more pasteurization step(s), subjection to one or more emissions of particular radiation such as γ radiation or X-rays or a combination of these methods. Among the active products capable of being added to blood products, there may be mentioned in particular agents which protect against free radicals (vitamin C and the like) and betapropiolactone which causes a phenomenon of alkylation of proteins or combined with physical treatment such as nanofiltration by means comprising pores of less than 75, 35 or 15 nm (Asahi, Millipore, Planova, Pall, . . . ). Such products should be used at doses which do not cause a toxicity phenomenon or denaturation of the treated blood products. However, at the irradiation doses used according to the invention, the addition of such products is not necessary in order to cause inactivation of nonenveloped viruses or to ensure protection against free radicals, even for cells treated.

The method of viral inactivation of the invention may be combined with a general method of isolating or separating blood derivatives from whole blood.

This method may comprise one or more filtration, precipitation or chromatographic separation step(s) and the like which make it possible to separate the various components of whole blood from each other.

According to the invention, most of the emission of UVC radiation occurs between about 250 and about 270 nm, preferably at the wavelength of about 254 nm, that is to say the preferred region of absorption of nucleic acids.

Therefore the method of viral inactivation, preferably the method of inactivity present in a blood-product, comprising the use of irradiation dose of ultraviolet radiation received by the blood product lower than 640 joules/m$^2$ (but higher than 2 joules/m$^2$). Preferably the irradiation doses received by the blood products are comprised between about 5 or about 10 joules/m$^2$ and about 500 joules/m$^2$, more preferably between about 200 joules/m$^2$ and about 450 joules/m$^2$, more particularly between about 230 joules/m$^2$ and about 400 joules/m$^2$.

Advantageously, the method according to the invention comprises a step of flowing the blood product past one or more emissions of UVC radiation (type C-ultraviolet radiation), while controlling the flow of the blood product such as the radiation doses of ultraviolet radiation which are received by said blood product, are lower than 640 joules/m$^2$, preferably in the range above described, while the blood product is substantially free of non-envelopped viruses and does not contain quenchers when said blood product is subjected to one or more emissions of type C-ultraviolet radiation.

The inventors have also discovered unexpectedly that it is possible to use said efficient UVC-radiation upon various blood products, while maintaining most of their proteinic activity.

According to the type of blood product treated and to the type of activity bio-assay used, it is possible to test which percentage of activity will be remain after UVC treatment. Said percentage of activity will be advantageously higher than 65 or 70%, preferably higher than 75% and more preferably higher than 80% or 85% or higher than 90% or 95% (the activity of the product not treated will be about 100%).

It is important to note that this percentage can vary a lot according to the blood product treated, but also according to its concentration. The remaining activity is easily characterised for the main blood products such as coagulation factors, but could not be characterised for some specific blood products, such as albumin, immoglobulin, whole blood or cellular compounds.

However, the inventors have observed unexpectedly that the UVC-radiation treatment according to the invention is sufficient to allow an efficient elimination of the viral components presented in said blood products, especially non-envelopped viruses and possibly envelopped viruses.

This method is also easy and safe to be used and does not require the addition of possible toxic compounds, such as quenchers, but could be combined with the addition of compounds such as the one above-mentioned (vitamin C), allowing a protection of the proteinic elements and cellular components present in said blood product against free radicals.

Therefore, the method according to the invention, allows that the radiation doses received by the treated blood product affect essentially the nucleic acid sequences of the viruses, resulting in disrupting and alterating of their nuclear structure.

Unexpectedly, the Inventors have observed that it was also possible to treat blood products not only in thin layers ("monolayers" or so-called laminar layers) or otherwise, that is to say that there are no limiting factors for the volumes treated. This property is particularly advantageous, because by treating blood products which are not in thin layers, it is possible to avoid the disruption phenomena which exist at the solid/liquid surface when the work is carried out in thin layers. In addition, by not working in thin layers, it is possible to treat large quantities of blood products and to avoid problems of heating, shearing and heterogenity of the blood product treated (BAILEY et al., Biochemical Engineering Fundamentals, Vol. II., McGraw-Hill Book Company, 1986).

The wavelength of emission of UVC radiation and the irradiation doses can be adjusted by the person skilled in the art according to the quantity and type of blood products to be treated. However, in order to reduce the phenomenon of denaturation of the blood product, the person skilled in the art may adjust the irradiation doses of the UVC emission wavelength so as to reduce the denaturation and the possible loss of activity of the said blood products. This adjustment will be made so as to be in accordance with the European CPMP standards (CPMP/BWP268/95 and 269/95 rev 2).

It is possible to obtain complete viral inactivation of the non enveloped viruses, especially the parvoviruses present (that is to say that it is no longer possible to identify viruses above the detection threshold) while limiting the irradiation doses received and allowing a reduction in loss of activity of the said product of less than 30–5%, preferably less than 15–5%.

Another aspect of the invention concerns a device or apparatus for the viral inactivation of a blood product, comprising an emitter of type C-ultraviolet array, placed as if to emit the ultraviolet radiation towards the blood product to be treated and placed in a quartz tube or tube made of polymerized material which generally does not absorb in the region of wavelength emitted by type C-ultraviolet radiation and a flow meter controlling the flow rate of the blood product to be treated.

The device or apparatus according to the invention is also not limited to the dose of irradiation used in the method according to the invention and could be used in order to inactivate strongly all the viral elements present in said blood product, even if it may affect the activity of the protein or cellular components comprised therein or softly the cellular components of a blood product to obtain the apoptosis of the cells present in said blood product.

Possibly, the flowmeter, may be integrated directly in the (digital) pump (Watson® pump).

Said device or apparatus presents the advantages of being simple and easy to be used and could be combined with classical and industrial separation units of blood products. In addition, it does not necessarily need an additional unit for the purification of the blood products in order to remove any addition of possible toxic, chemical components (such as quenchers).

The device or apparatus according to the invention essentially comprises an emitter of type C-ultraviolet arrays, that is to say an emitter whose array length is essentially between about 230 and about 270 nm, preferably at the wave length of the order of 254 nm, which is the maximum region of absorption of ultraviolet array by nucleic acid of the virus to be treated in a blood product.

The device or apparatus according to the invention allows the emission of irradiation doses (to be received by the blood product) of between about 2 joules/m$^2$ and about 2000 joules/m$^2$, preferably lower than 640 joules/m$^2$ (which are advantageously the efficient dose of irradiation in order to obtain the inactivation of non-developed viruses present in said blood product), more preferably irradiation comprised between about 200 and about 500 joules/m$^2$, more preferably between about 240 and about 400 joules/m$^2$.

Therefore, the device or apparatus according to the invention is not limited by the dose of radiation to be received by the blood products and the possible percentage of proteinic inactivation of the blood products to be treated. (However, if the concentration is higher, it is also necessary to increase the irradiation dose (Beer-Lambert Law).

This apparatus also comprises devices which ensure the isolation or the separation of blood derivatives from whole blood.

These devices may comprise means for a precipitation, centrifugation/decantation, filtration, concentration or dialysis of the blood product to be treated which can be adjusted by the person skilled in the art according to the blood products to be separated and treated.

The device or apparatus may also comprise means allowing the addition, to the blood product(s), of an agent which protects against free radicals capable of being generated by the ultraviolet radiation. Such agents may consist of vitamins such as sodium ascorbate, glutathion, or other products (SOD) well known to the person skilled in the art. In addition, the apparatus may also comprise means allowing the addition, to the blood product, of various chemical compounds capable of inactivating certain contaminants present in the blood products to be treated. These compounds may be in particular products which become active under ultraviolet radiation and which are capable of being combined with the method of the invention so as to obtain a synergistic effect on other contaminants present in the said blood product(s).

Another aspect of the present invention is related to a method for treating a mammal patient, including the human, suffering from an hyper-proliferative disorder, such as a leucemie, said method comprising the steps of:

obtaining a blood product from said patient and comprising a cellular component selected from the group consisting of lymphocytes, monocytes or a mixture thereof, in order to obtain their apoptosis,
  separating from said blood product specific cells which are not able to be affected by said disorder (for instance erythrocytes, thrombocytes, etc),
  flowing the blood product comprising said cells to pass one or more emissions of UVC radiations (type C ultraviolet radiation), while controlling the flow of the blood product such as the radiation doses of the ultraviolet irradiation which are received by said blood product are higher than about 2 joules/m$^2$ and lower than about 50 joules/m$^2$ preferably comprised between about 5 and about 20 joules/m$^2$, and preferably said blood product does not contain quenchers when said blood product is subjected to one or more emissions of said C ultraviolet irradiation and
  (possibly) the step of reinjecting said blood product to the patient.

The present invention also relates to the blood product obtained by the method of the invention free of viral contaminants, in particular, free of nonenveloped (single-stranded or double-stranded DNA or RNA) viruses, particularly parvoviruses such as parvoviruses B19 and/or H1, said blood products, in particular blood derivatives such as clotting factors, being characterized by an initial activity of more than 70%, 75%, 80% or 85%, preferably more than 95%.

A final aspect of the present invention relates to the pharmaceutical and/or cosmetic composition (such as a biological adhesive) comprising said blood product(s). The present invention will be described in details in the following non limiting examples with reference to the enclosed figures.

DESCRIPTION OF A PREFERRED EMBODIMENT OF THE INVENTION

Figure 1:
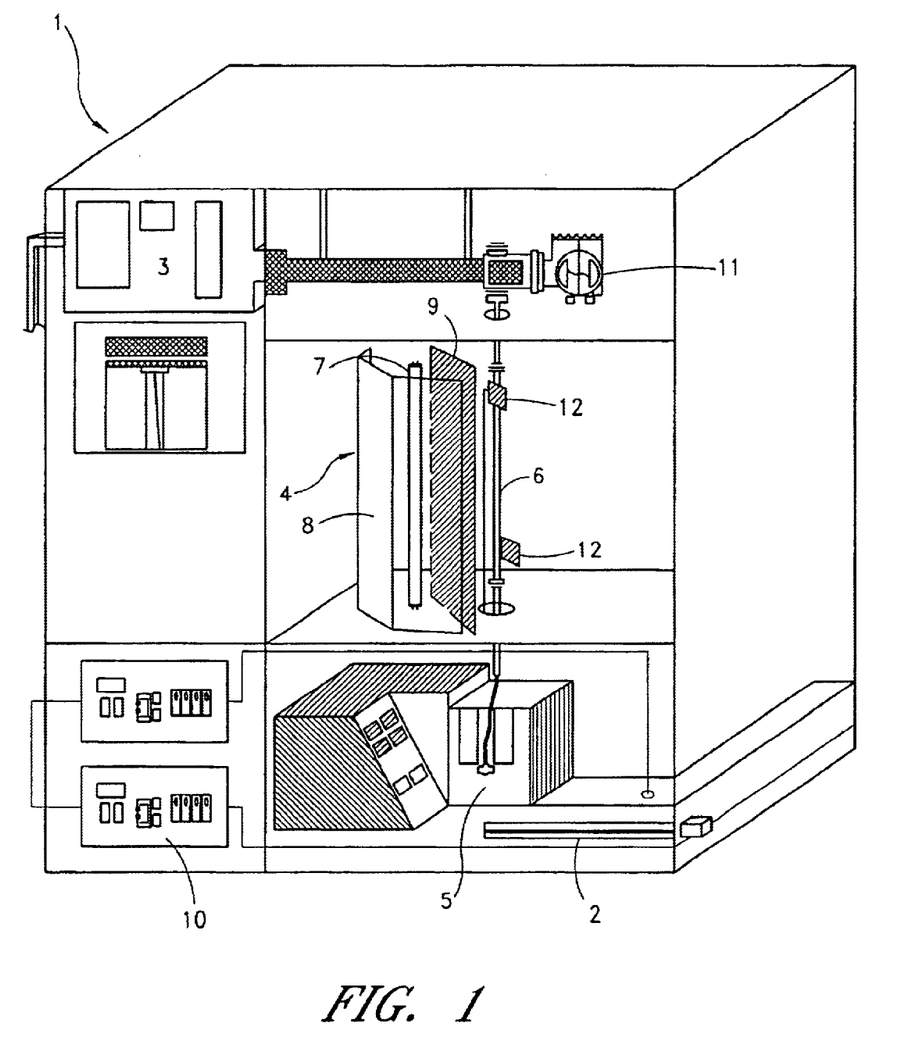
FIGS. 1 and 2 represent schematic examples of apparatus according to the present invention.
Figure 2:
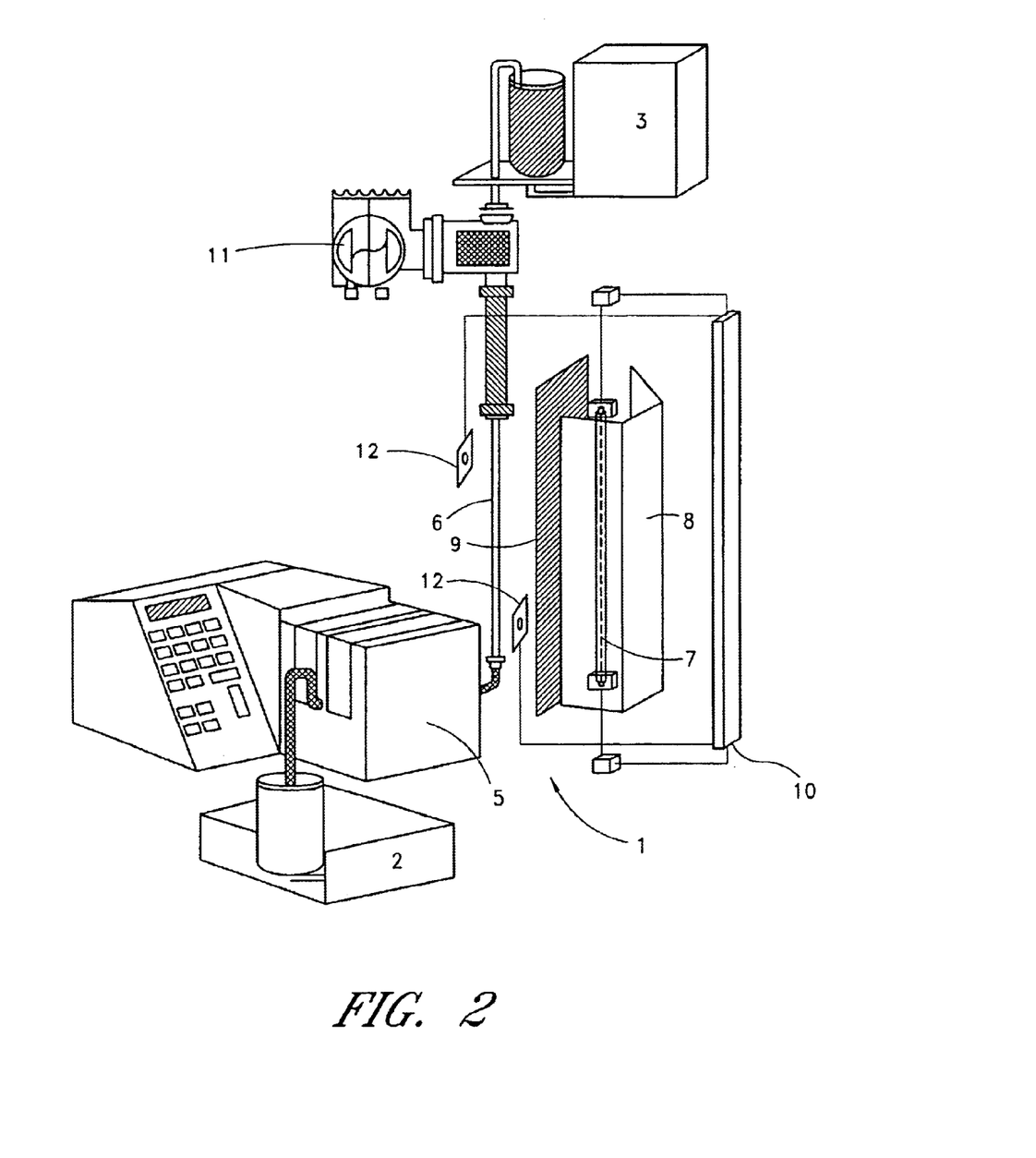
Figure 3:
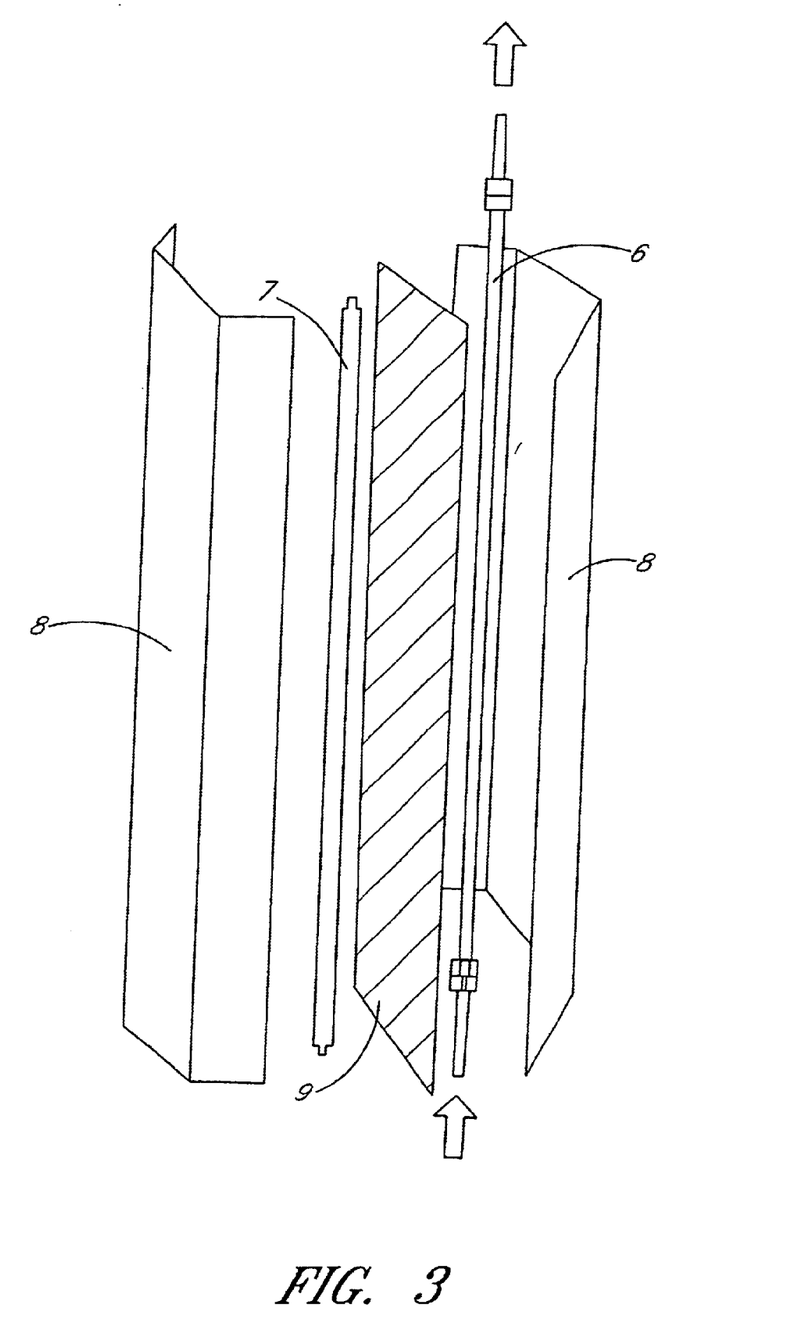
FIG. 3 represents a schematic detail of the apparatus according to the present invention.

In FIGS. 1 to 3, an apparatus for the preparation of a blood product according to the invention is represented.

This apparatus 1 comprises devices (2, 3) which bring about in particular precipitation, centrifugation/decantation, filtration, concentration and dialysis of blood products such as factor VIII or fibrinogen, and which can be adapted by persons skilled in the art according to another blood product treated.

This apparatus also comprises the device 4 according to the invention which brings about, by a physical treatment, viral inactivation of the said blood product.

The blood product according to the invention is brought by a pump in a quartz tube 6 to the device 4.

This device comprises a UV lamp 7, preferably of disinfection UV tube type, in which more than 90% of the emission occurs between 230 and 270 nm, preferably at a wavelength of the order of 254 nm, this lamp being mounted in a reflecting chamber 8, cylindrical or otherwise, which sends the radiation towards the quartz tube 6 placed at the focus of the reflecting chamber 8.

In the device of the invention, no contact is possible between the product circulating in the quartz tube 6 and the UV lamp 7.

A system for static or dynamic turbulence, such as baffles, an injection of nitrogen, a mechanic or magnetic turbine make it possible to maintain a homogeneous flow in the quartz tube 6.

Such system may comprise for instance an element turbine made of baffles disposed in the centre of the tube homogenising the flow of the blood product in the centre of the tube and allowing that the blood product present in the tube is treated by UVC radiation in a uniform way.

The apparatus also comprises a pump 5 and a flow meter 11 (possibly combined) which makes it possible to control the flow rate of the blood product to be treated and to vary the passage time of the blood product in front of the UV lamp 7.

In addition, the device may comprise one or more screens or filters 9 placed between the quartz tube 6 and the UV lamp 7. The appropriate choice of screens makes it possible to vary the irradiation doses received by the blood product to be treated and the specific choices of emitted wavelengths. It is also possible to vary the irradiation doses received by the blood product to be treated by adjusting the choice of the UV lamp used (it being possible to use different lamp powers), by selecting the screens used and by adjusting the flow rate of the blood product passing in front of the lamp. These modifications can be adjusted by persons skilled in the art according to the quantity and type of blood product treated. Furthermore, a system 10 for controlling the quantity of ultraviolet C which irradiates the quartz tube 6 (and therefore the irradiation dose received by the blood product) is placed on the opposite side relative to the UV lamp 7.

This control system comprises, as represented in the figures, one or more sensor(s) 12 advantageously placed on either side of the quartz tube 6 and optionally on either side of the screen 9, so as to enable persons skilled in the art to adjust the rate of flow of the blood product according to the type of blood product to be treated and according to the irradiation doses emitted by the UV lamp 7.

The residence time of the blood product may be adjusted in order to obtain a constant dose of irradiation. The diameter of the tube may be adjusted to the volume to be treated as well as the power or the length of the disinfection lamp. The temperature is controlled and recorded both inside the device and in the fluid (blood product).

The apparatus and the device according to the invention may also comprise means for controlling the temperature of the blood products, which may consist of cooling means such as a refrigerating device or a fan.

The various materials used in the device and the apparatus according to the invention are advantageously essentially disposable products such as stainless steel 316L, Teflon, and the like, which are in agreement with good pharmaceutical manufacturing practice (GMP or CIP and SIP) and which can be hygienically treated on site.

The device for viral inactivation by ultraviolet C radiation is advantageously placed downstream of the general method for treating and separating a blood product, for example before sterilizing filtration or after ultrafiltration of the blood product. The simplicity and the small size of the portable device of the invention advantageously allows its use for the inactivation of any type of blood product without considerably modifying an apparatus for the preparation, purification or separation of blood products.

The device and the apparatus according to the invention can be constructed in a single block or as juxtaposed portable modules placed in series or in parallel. The irradiation doses received by the blood product treated are particularly low and vary between 2 and 2000 joules/m$^2$ and are preferably of the order of 230 to 400 joules/m$^2$. Unexpectedly, these irradiation doses are sufficient to obtain the desired viral inactivation.

The power of the ultraviolet lamp is advantageously preferably between 4 and 132 Watt, preferably between 8 and 60 Watt, so as to preserve the integrity of the products treated. It should be noted that, using the method of the invention, the activity of the blood product (in particular of clotting factors, fibrinogen or immunoglobulins) is not greatly affected (on average less than 5% reduction in activity).

The UV lamp used in the apparatus according to the invention is preferably of SPA® type, in particular that produced by the company AQUAFIN VALENCIA (California, USA).

In the following examples, various measurements of viral inactivation which are obtained on samples of blood products infected with parvoviruses and other enveloped or nonenveloped viruses (HAV) are given.

EXAMPLES

1. Materials and Methods

Because of the problems caused by the use of certain human parvoviruses and the problems of culturing these parvoviruses, in particular parvovirus B19, in vitro, the murin parvovirus MVMp, which has a very similar size and shape, is used as model for developing methods allowing the inactivation of parvovirus B19. The murin parvovirus MVMp was chosen because this type of parvovirus is less sensitive than parvovirus B19 to inactivation by ultraviolet radiation or by temperature modification.

The tests are compared to the inactivation of a nonenveloped RNA virus.

EMC (encephalomyocarditis) is a member of the Picornaviridae family, whose inactivation has been studied as model of nonenveloped RNA virus. The EMC virus is a murin virus which can be used as model of contamination with the hepatitis A virus in man. $10^6$ pfu/ml for EMC and $10^{10}$ pfu/ml for MVMp are inoculated into various samples of blood product (cryoprecipitate, factor VIII or immunoglobulins).

2. Measurement of Active Virus Titre

The virus reduction index was determined according to the recommendations of the European Communities (EEC Regulatory Document not for guidance, Biologicals 1991, 19, p. 251) and expressed as logarithmic reduction. The measurements of titre can be carried out according to the methods described by Tattersall P. (J. Virol., 10, pp., 586–590 (1972)) and by Russell S. J. et al. (J. Virol., 66, pp. 2821–2828 (1992)).

The cell lines chosen to be infected with the parvoviruses are the NB324/k human cell line (described by Tattersall et al.) and the L929 line (clone 929 of the A9 ATCC CCL 1.4 line).

The titration is carried out by in situ hybridization of the infectious centres (replicative centres) with the use of a radioactively labelled probe. The detection is carried out on nitrocellulose filters. The determination of the virus titre can be carried out by lysis plaque or by limiting dilution method ($TCID_{50}$—Sperman-Karber method).

The blood products treated by the method of the invention are a cryoprecipitate of plasma, factor VIII, previously treated or otherwise by addition of solvent/detergent, fibrinogen and immunoglobulins.

3. Results

The method (each step) and the apparatus of the invention comply with the requirements of the validations required by the European authorities (CPMP/BWP/268/95 and CPMP/BWP/269/95 rev 2 respectively operational from 14 Aug. and 13 Sep. 1996 (incorporated herein by reference)). In accordance with the recommendations of these authorities (§ 5.2.1 (1) CPMP/BWP/269/95), the method and the apparatus of the invention comprise at least one operating step of effective treatment against nonenveloped viruses, in particular parvovirus B19 (§ 5.2.2 (iii)). The invention meets in particular the requisite inactivation requirements, namely 5 to 9 log reduction (cf. Annex I CPMP/BWP/268/95), that is to say that it is possible to eliminate all the inoculated viruses. Indeed, the Inventors did not observe, after treatment, any virus multiplication above the detection threshold.

Figure 4:
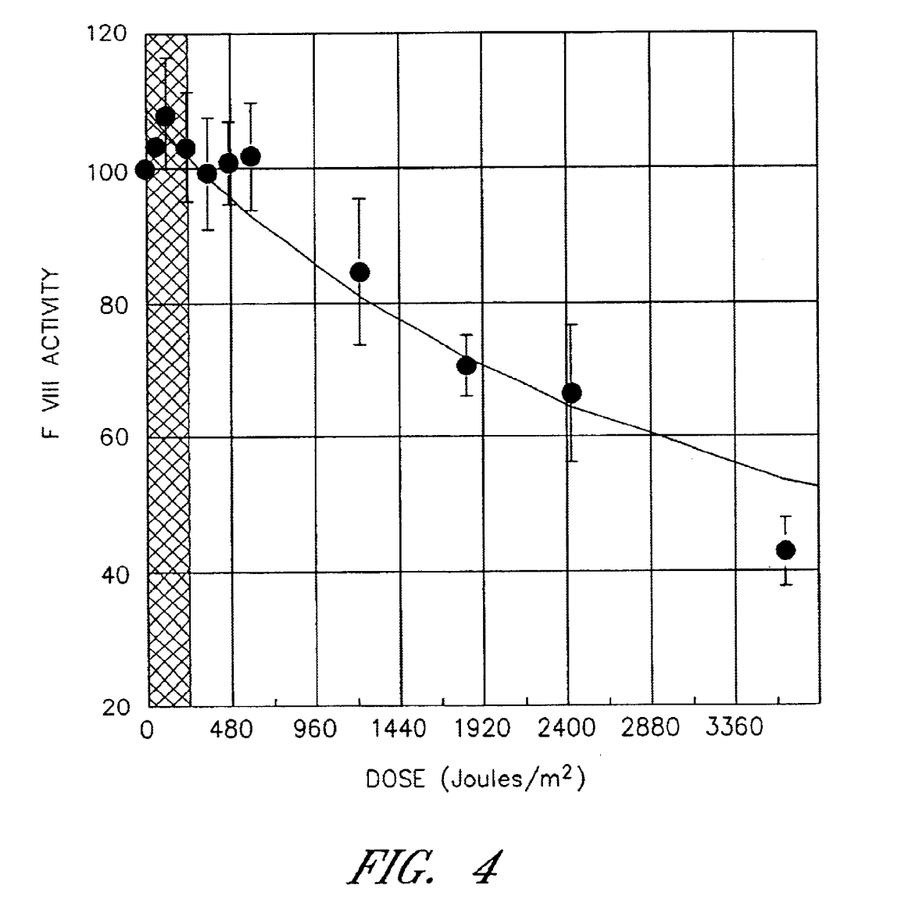
FIG. 4 represents the percentage of preserved factor VIII activity measured in chromogenic medium as a function of increasing irradiation doses of ultraviolet rays received by factor VIII.
Figure 5:
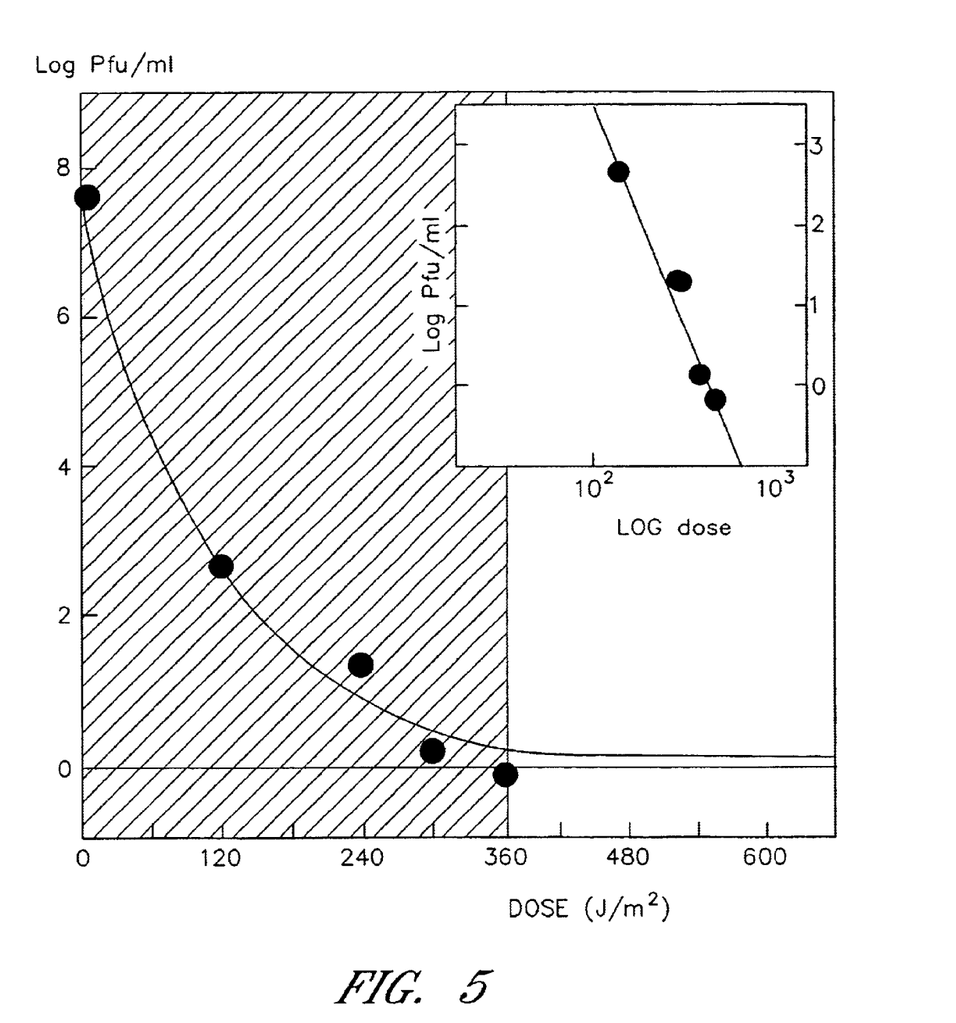
FIG. 5 represents the titration of the parvovirus MVMp inoculated into a solution of factor VIII treated at increasing irradiation doses of ultraviolet rays, the irradiation doses being the doses received. This measurement is also represented by giving the logarithmic values.

As indicated in FIG. 4, increasing doses of ultraviolet radiation cause inactivation of blood derivatives such as factor VIII. However, the Inventors unexpectedly observed that it is possible to obtain inactivation of parvoviruses by irradiation, by means of ultraviolet C radiation, of the viruses inoculated into solutions comprising factor VIII, while limiting the irradiation doses, without substantially affecting the activity of the blood derivatives (see FIG. 5).

In Table 1 below, a logarithmic reduction ($\log_{10}$) of the viruses inoculated into a composition comprising immunoglobuline is observed. These logarithmic reduction values are given for increasing doses of irradiation by ultraviolet C radiation which are received by the said immunoglobulins.

Figure 6:
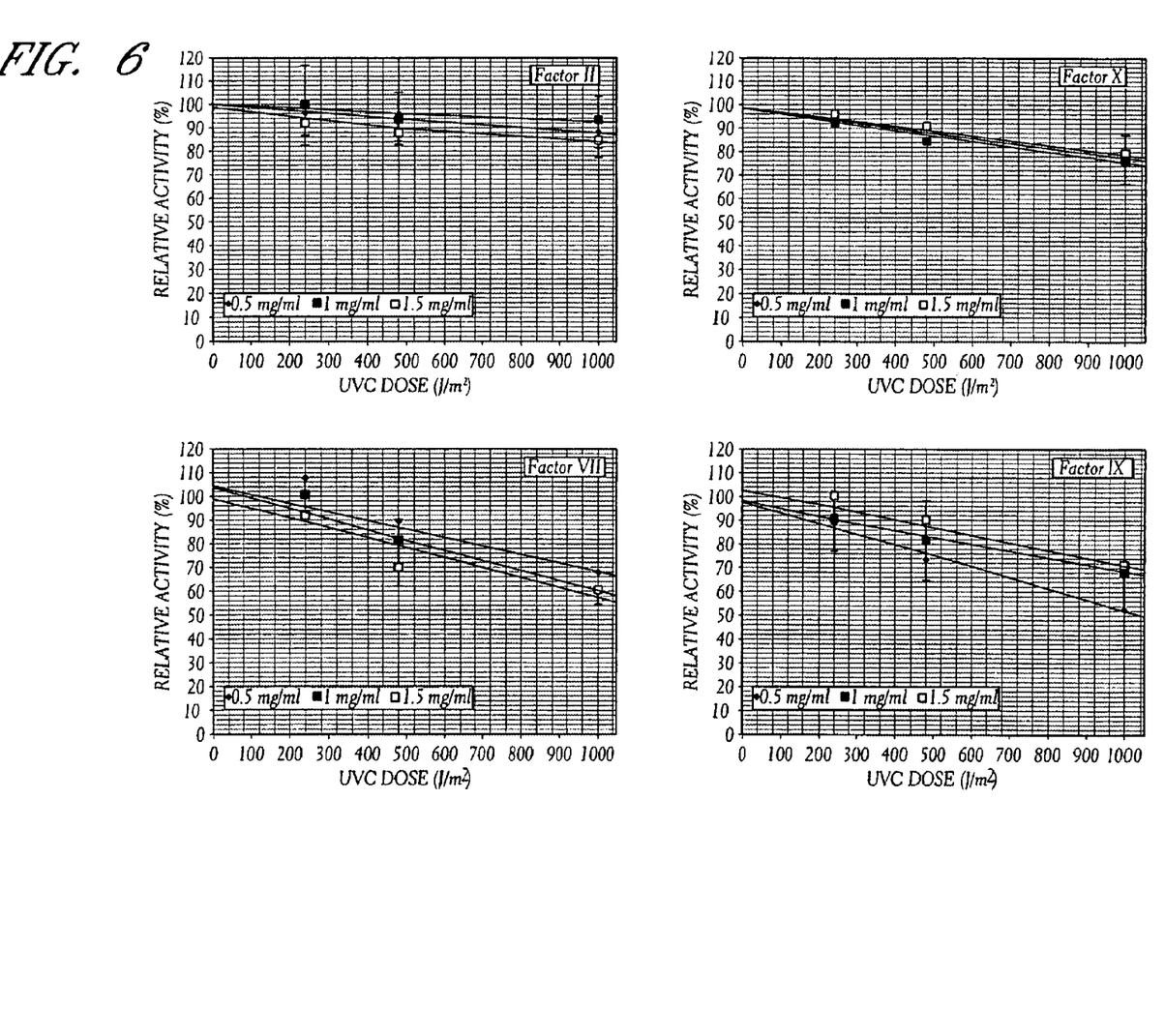
FIG. 6 represents the decrease of the relactive activity of various coagulation factors (factor II, factor VII, factor IX and factor X) at various concentrations with increased doses of UVC treatment.

The enclosed various results (FIG. 6) show the decrease of the percentage of relative activity of various coagulation factors present at different concentrations in the photoreactor submitted to increased UVC irradiations (in PBSB).

It is important to note that at 480 joules/m$^2$, reduction factor for canin parvovirus is higher than 5.5 log and the reduction factor for HAV is higher than 4.4 log.

The inventors have also observed that the UVC irradiation doses used according to the present invention allow a partial inactivation of other viruses, including enveloped viruses, and could be therefore used advantageously with other inactivation processes in order to obtain a synergic effect upon all types of viral infections.

TABLE I

| VIRUS TYPE | | REDUCTION FACTOR ($Log_{10}$) | | | |
|---|---|---|---|---|---|
| | ENVELOP | FVIII | ALBUMIN | IMMUNOGLOBULIN | FIBRINOGEN |
| $MVP_P$ | – | >7 | >7 | >7 | >7 |
| EMC | – | 6.4 | 6.4 | 6.4 | 6.4 |
| BHV | + | 2.58 | 2.5 | 3 | 2.6 |

What is claimed is:

1. A method of inactivating nonenveloped viruses present in a blood product, comprising
   flowing the blood product in the absence of quenchers past one or more emissions of type C ultraviolet radiation; and
   controlling the flow of the blood product in the flowing step such that the irradiation dose of ultraviolet radiation received by the blood product is lower than 640 joules/m$^2$,
   wherein the resulting blood product is substantially free of nonenveloped viruses.

2. The method according of claim 1, wherein the irradiation doses of ultraviolet irradiation which are received by the blood product are between about 10 joules/m$^2$ and about 400 joules/m$^2$.

3. The method of claim 1, wherein the blood product is selected from the group consisting of whole blood and cellular compounds.

4. The method of claim 3, wherein the blood product is selected from the group consisting of platelets and erythrocytes.

5. The method according to claim 1, wherein the blood product is selected from the group consisting of serum, plasma and blood protein compounds.

6. The method of claim 5, wherein the blood protein compounds are clotting factors selected from the group consisting of factor VIII, factor IX, von Willebrand's factor, fibrinogen, fibronectin and a mixture thereof.

7. The method of claim 5, wherein the blood protein compounds are selected from the group consisting of immunoglobins, albumin, thrombin, ATIII anti-thrombin, lymphokines LDL and interferons.

8. The method of claim 1, wherein most of the emission of type C ultraviolet radiation occurs between about 250 and about 270 nm.

9. The method of claim 1, wherein most of the emission of type C ultraviolet radiation occurs at a wavelength of the order of 254 nm.

10. The method of claim 1, wherein the method is combined with one or more other physical or chemical viral inactivation treatments.

11. The method of claim 10, wherein the other methods of viral inactivation are physical or chemical viral inactivation treatment methods selected from the group consisting of one or more dry or wet heating step(s), nanofiltration, the addition of chemical components, one or more pasteurization step(s), subjection to one or more emission(s) of particular radiations and a combination of these methods.

12. The method of claim 11, wherein the emission of particular radiations is selected from the group consisting of γ radiation and X-ray radiation.

13. The method of claim 1, wherein the method is combined with a general method of isolating or separating blood derivatives from whole blood.

14. The method of claim 1, wherein the blood product is not treated in thin layers.

15. An apparatus for viral inactivation of a blood product comprising an emitter of type C ultraviolet rays placed so as to emit the type C ultraviolet radiation towards the blood product to be treated and placed in a quartz tube or a tube made of a polymerized material which does not absorb type C ultraviolet radiation, and a flow meter controlling the flow rate of the blood product to be treated.

16. The apparatus of claim 14, wherein the emitter is a UV lamp, with a power higher than 4 Watt.

17. The apparatus of claim 15, wherein the type C ultraviolet rays have a wavelength between about 250 and about 270 nm.

18. The apparatus of claim 15, wherein the irradiation doses received by the blood product are lower than 640 joules/m$^2$.

19. The apparatus of claim 15, further comprising a reflecting chamber sending the type C ultraviolet radiation towards the blood product to be treated.

20. The apparatus of claim 15, further comprising a system for controlling the does of ultraviolet C radiation which irradiates the blood product to be treated.

21. The apparatus of claim 15, further comprising a system for controlling the temperature of the blood product to be treated.

22. A method of treatment of a mammal patient suffering from a hyper-proliferative disorder affecting his blood cells, said method comprising the steps of:
   obtaining from said mammal the blood product comprising said cells;
   separating from said blood product the specific cells not affected by said disorder, and
   flowing the blood product in order to pass one or more emissions of (type C ultraviolet radiation), while controlling the flow of the blood product such as the radiation doses of the ultraviolet irradiation which are received by the blood product are comprised between about 2 and about 50 joules/m$^2$, in order to obtain the apoptosis of said blood cells.

23. The method according to claim 22, wherein the radiation doses of ultraviolet irradiations which are received by the blood product are comprised between about 5 and 20 joules/m$^2$.

24. The method according to claim 22, wherein the blood cells are selected from the group consisting of monocytes or lymphocytes.

25. A blood product produced according to the method of claim 1, wherein the blood protein compounds have retained more than 75% of their activity.

26. The blood product according to claim 25, wherein the blood protein compounds have retained more than 80% of their activity.

27. The blood product according to claim 25, wherein the blood protein compounds have retained more than 85% of their activity.

28. The blood product of clam 25, which is selected from the group consisting of serum, plasma, and blood protein compounds.

29. The blood product of claim 25, which is selected from the group consisting of clotting factors, factor VIII, factor IX, von Willebrand's factor, fibrinogen, fibronectin and a mixture thereof.

30. The blood product of claim 25, which is selected from the group consisting of immunoglobulins and albumin.

31. The method of claim 22, further comprising the step of reinjecting said blood product to the patient.

* * * * *

UNITED STATES PATENT AND TRADEMARK OFFICE
CERTIFICATE OF CORRECTION

PATENT NO. : 6,833,108 B2  
DATED : December 21, 2004  
INVENTOR(S) : Ruth Laub et al.

It is certified that error appears in the above-identified patent and that said Letters Patent is hereby corrected as shown below:

<u>Column 12,</u>  
Line 22, delete "does" and insert -- dose --.  
Line 35, delete "(type C ultraviolet radiation)" and insert -- type C ultraviolet radiation --.  
Line 56, delete "clam" and insert -- claim --.

Signed and Sealed this

Fourth Day of April, 2006

JON W. DUDAS  
*Director of the United States Patent and Trademark Office*